United States Patent [19]

Schreibman

[11] Patent Number: 4,976,694

[45] Date of Patent: Dec. 11, 1990

[54] APPARATUS AND METHOD FOR PREVENTING INFECTION

[76] Inventor: Gary Schreibman, P.O. Box 2746, La Mesa, Calif. 92041

[21] Appl. No.: 284,699

[22] Filed: Dec. 15, 1988

[51] Int. Cl.$^5$ .................... A61M 37/00; A61M 1/00; A61B 10/00
[52] U.S. Cl. .................................. 604/140; 604/131; 604/319; 128/749; 128/752
[58] Field of Search ........ 606/203; 128/749, 752–754, 128/763, 765, 768; 604/4, 73–76, 32, 35, 37, 38, 313–316

[56] References Cited

U.S. PATENT DOCUMENTS

| | | | |
|---|---|---|---|
| 2,103,174 | 12/1937 | Posada | 606/203 |
| 3,815,579 | 6/1974 | Rose | 604/73 |
| 4,008,717 | 2/1977 | Kowarski | 128/768 |
| 4,693,257 | 9/1987 | Markham | 128/752 |
| 4,796,644 | 1/1989 | Polaschegg | 128/765 |

Primary Examiner—Ronald Frinks
Assistant Examiner—Robert Clarke

[57] ABSTRACT

Process and apparatus for quickly removing contaminated tissue and blood from a localized skin wound in the body of a human being immediately after contamination has occured by removing all of the tissue from the wound by use of a biopsy punch and removing the contaminated blood from the wound by suction from a vacuum pump.

5 Claims, 4 Drawing Sheets

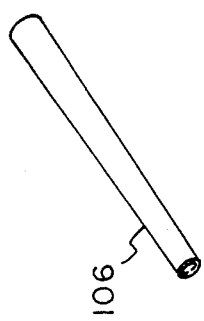
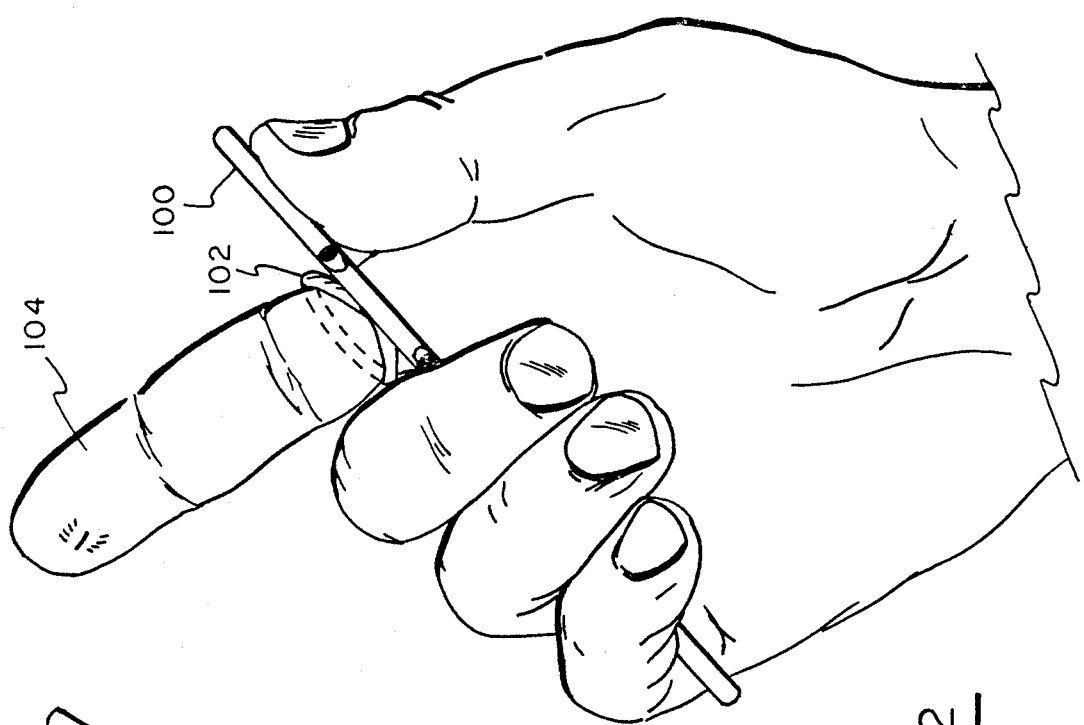
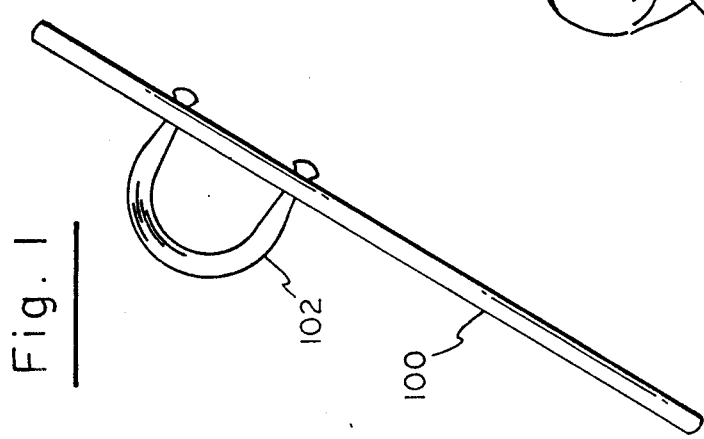

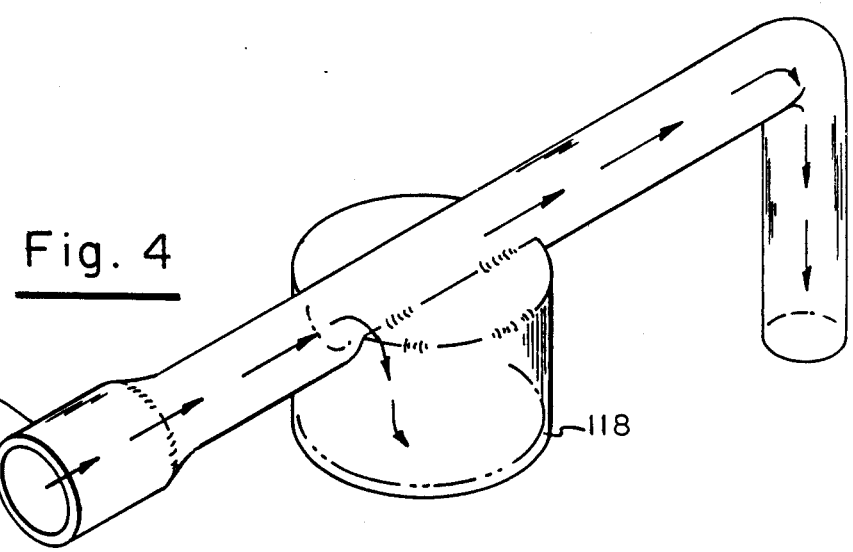
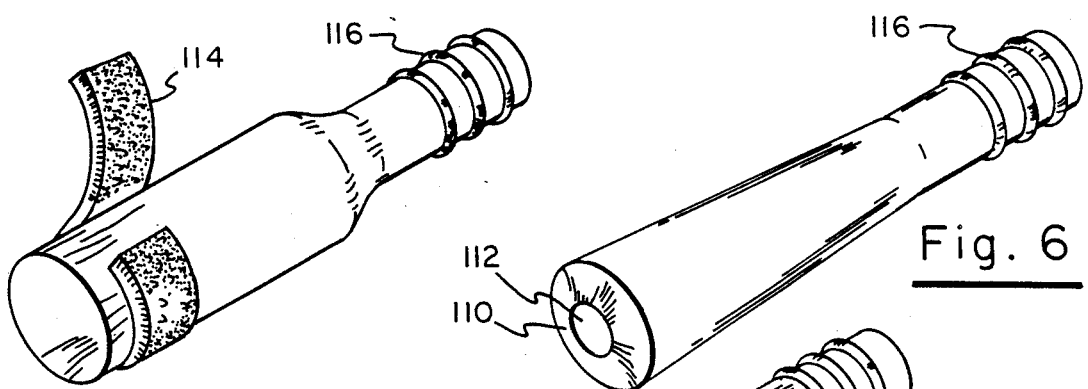
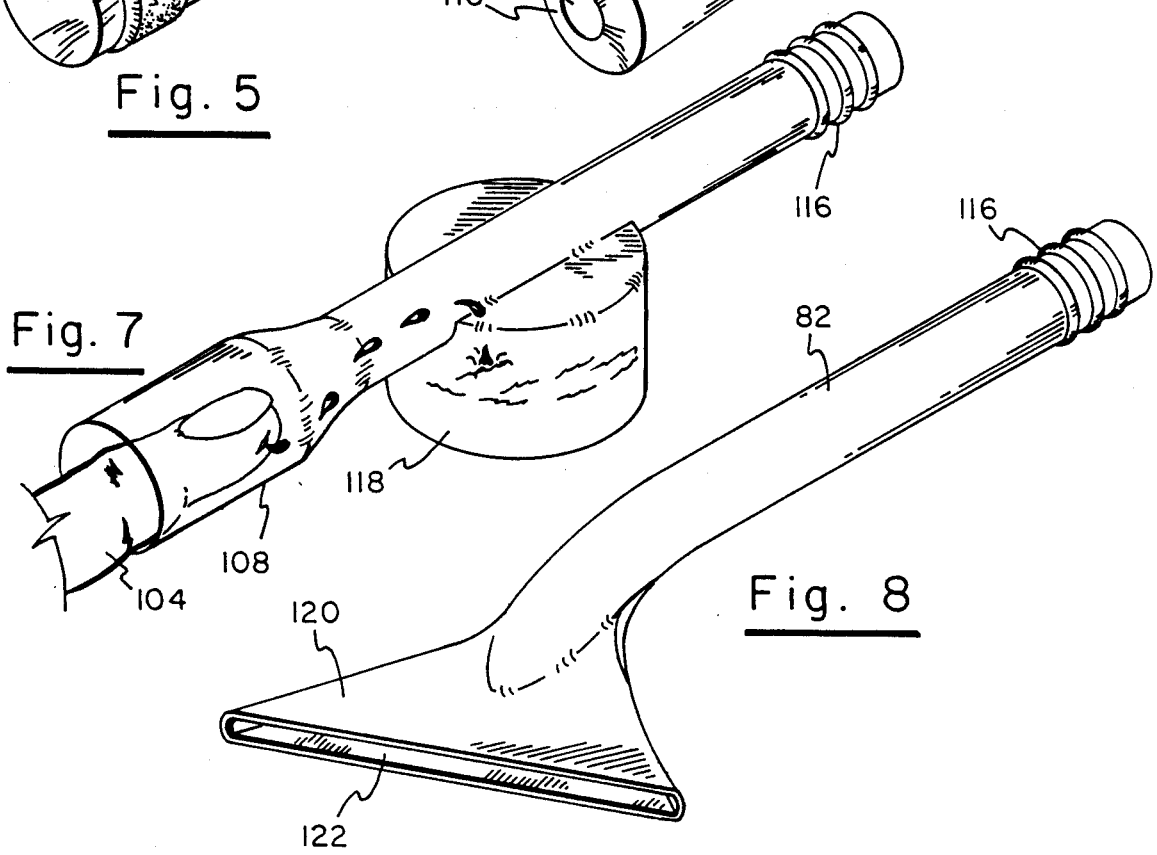

APPARATUS AND METHOD FOR PREVENTING INFECTION

BACKGROUND OF THE INVENTION

It is well known that almost all individuals at one time or another are subject to accidentally or purposefully opened skin wounds produced by punctures, lacerations, incisions, abrasions or the like. Such wounds are normally treatable by first cleaning the wound, then applying iodine or the like and then bandaging the wound. However, surgeons, medical workers, police, firemen, paramedics and individuals engaged in other such occupations are subjected to such wounds under conditions wherein there is great risk of dangerous and even fatal viral infection by seroconversion from contaminated needles, cuts by broken glass and even intentional bites from diseased individuals being treated or placed into custody. Hepatitis B and HIV or AIDs virus are well known causes of such viral infections. In order to eliminate any risk of infection, it is necessary to remove all contaminated tissue and blood from the wound as quickly as possible.

SUMMARY OF THE INVENTION

It is an object of the present invention to provide new apparatus and methods for quickly removing contaminated tissue and blood from a localized skin wound in the body of a human being immediately after contamination has occured.

Another object is to provide new apparatus and methods of the character indicated which can be operated easily, quickly and effectively by operators who require only a minimum of training before putting the apparatus and methods into use.

Still another object is to provide new apparatus of the character indicated which is durable, portable and relatively inexpensive.

In accordance with the principles of the invention, all of the tissue from the contaminated wound is removed using a biopsy punch. The contaminated blood is removed through use of a suction pump. When the wound is so positioned as to permit use of a tourniquet or the like, the tourniquet is secured in such manner as to effect vasoconstriction or hemostasis of the body between the heart and the region of the wound, thereby controlling blood flow to and from the region prior to removal of the tissue. Moreover, before the tissue is removed, the wound is copiously irrigated with one or more liquid preparations chosen to deal with the contamination. When there is risk of viral infections such as Hepatitis B or AIDS, a combination of liquids which are lethal to viruses and are thus viricidal is used. One known combination is a 50-50[or 1:1 ratio]10% solution of sodium hypochlorite [bleach] and O-phenyl phenol [lysol]. After the liquid flushing step has been carried out, a topical local anesthetic or freezing agent such as ethyl chloride spray, followed by local injection of plain lidocaine, should be applied to the region of the wound prior to use of the punch. The punch should be used in such manner as to remove a section of tissue larger and deeper than the possibly contaminated wound region.

The open wound should then be flushed with the same liquid preparations as originally used. Then suction is applied via a vacuum pump to remove pathogenic microorganisms and any loose infected tissue. After the suction has produced sufficient bleeding, the tourniquet is fully released to cause a more profuse loss of blood. The tourniquet can then be reapplied, and the suction step repeated if necessary. A compression dressing can then be applied to the wound to stop the bleeding.

If the wound is so positioned that no tourniquet can be applied, the tourniquet operation is of course eliminated, but all other procedures are carried out sequentially as explained above.

The vacuum pump is connected detachable to the skin wound via first means such as a hose which has means at one end adapted for detachable suction tight engagement to the wound. Different first means can be used depending upon the location of the wound. When desired, all such first means can be connected to the pump via selection means such as a valve which enables the operator to select the particular first means desired for use.

All of the foregoing and still further objects and advantages of this invention will either be explained or will become apparent to those skilled in the art when this specification is studied in conjunction with the drawings submitted herewith.

BRIEF DESCRIPTION OF THE DRAWINGS

FIG. 1 is a perspective view of a finger tourniquet used in the invention.

FIG. 2 is a perspective view showing the tourniquet of FIG. 1 in use.

FIG. 3 is a perspective view of a biopsy punch used in the invention.

FIG. 4 is a perspective view of a thumb/finger suction thimble for use in the invention.

FIG. 5 is a perspective view of an alternate form of the thimble shown in FIG. 4.

FIG. 6 is a perspective view of another alternate form of the thimble shown in FIG. 4.

FIG. 7 illustrates the use of the thimble shown in FIG. 4.

FIG. 8 illustrates a hose attachment adapted for use for treating scratches and elongated cuts.

DETAILED DESCRIPTION OF PREFERRED EMBODIMENTS

Figure 13:
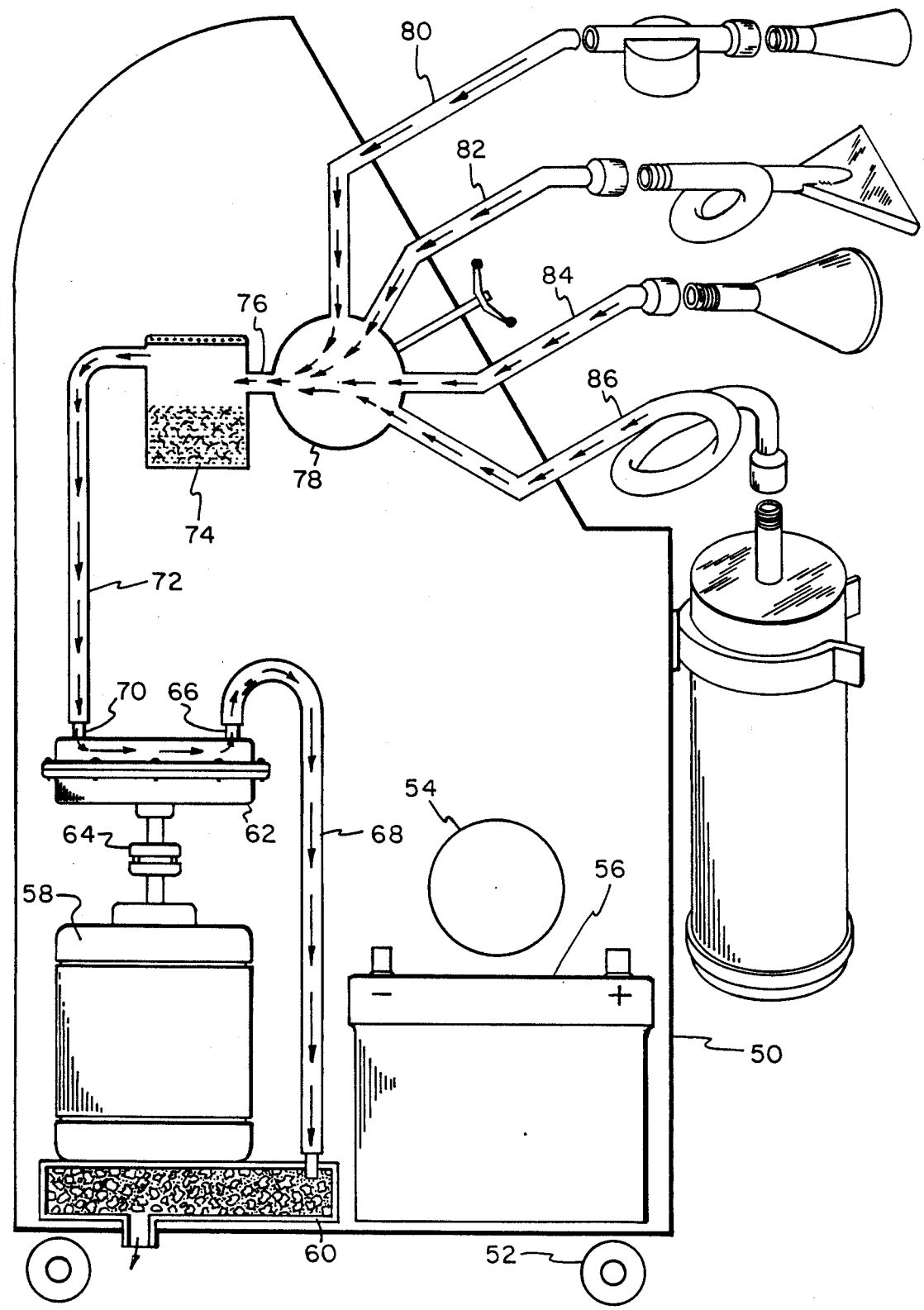
FIG. 13 illustrates the vacuum pump and associated components adapted for use in this invention.

Referring first to FIG. 13, a metal cart 50 or the like, movable on casters or wheels 52, supports a dc to ac power inverter 54 which connects a high output dc power supply 56, including storage batteries or the like, to an explosion proof electric motor 58. Disposed below the motor is a removable charcoal filter 60 which is vented to the atmosphere through an opening in the bottom of the cart. A vacuum pump 62 disposed above the motor and connected to the drive shaft thereof via a universal joint 64 has a discharge port 66 connected by tubing or hose 68 to filter 60. Pump 62 has a suction or intake port 70 connected by tubing or hose 72 through a second removable filter 74 to an inlet port 76 of a manually operable four way valve 78.

Figure 9:
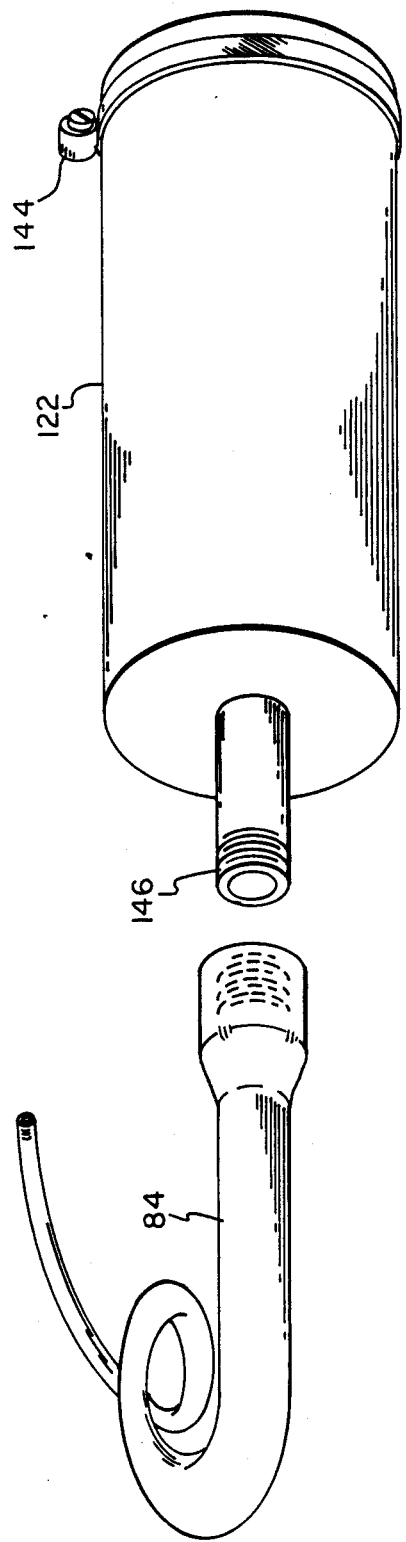
FIGS. 9, 10 and 11 are different views of a full arm suction attachment adapted for use in treating forearm or upper arm wounds.
Figure 12:
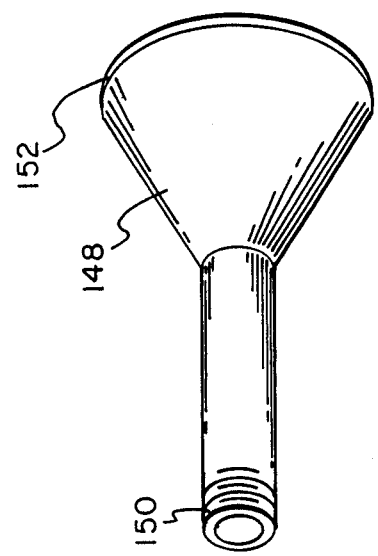
FIG. 12 illustrates a funnel suction attachment adapted for use in treating bite wounds.
Figure 11:
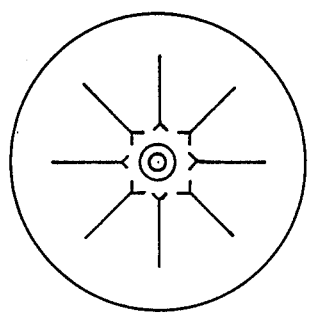
Figure 10:
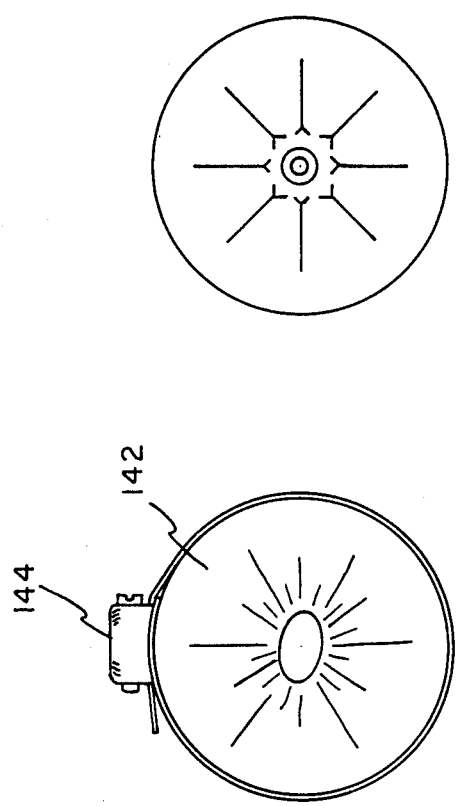

Depending upon the position of valve 78, suction forces can be applied through hose 80 to a finger/thumb suction thimble as shown in FIGS. 4-7, or through hose 82 to an attachment for treating scratches or cuts as shown in FIG. 8, or through hose 84 to the funnel attachment as shown in FIG. 12, or through hose 86 to the arm attachment as shown in FIGS. 9-11.

The vacuum system in addition to the two charcoal filters can contain a moisture trap. The cart can be a cabinet in the form of a cylindrical stainless steel sheet mounted on a square platform with a flat control panel that is covered by a protective dome of clear plastic. All components are explosion proof. The outside of the cabinet can have a disposable filter and a blood trap for determining the amount of blood which has been suctioned from the wound opening and for also conducting any type of blood analysis desired.

If a wound is in a thumb or finger, the finger tourniquet of FIGS. 1 and 2 can be used. The tourniquet is a bar 100 of aluminum or stainless steel or plastic provided with a loop 102 of heavy elastic material secured by spaced apart ends to the bar intermediate its ends. The loop is twisted about the finger 104 [which has the wound] tightly by rotating the bar and the bar is held in position by the other fingers. [The dimensions of this type of tourniquet can be varied to enable its use on other parts of the body.] After the wound is flushed with the desired liquid and the anesthetic is applied, a manually operated biopsy punch 106 of FIG. 3 [which can be spring loaded] is used to remove the tissue as explained above.

As shown in FIGS. 4-6, finger 104 can be inserted into a vacuum sealed end of a thimble conduit 108. This sealed end can be a tightly stretched latex membrane 110 with a small reinforced hole 112 for finger insertion which forms a tight seal, or this end can be flexible to be drawn vacuum tight when suction is applied. Another sealing method is to use a rubberized velcro-type external wrap 114 as a seal. The other end of the conduit can have "O" ring vacuum seals 116 for vacuum tight engagement with hose 80. The thimble can have a blood reservoir 118.

As shown in FIG. 8, hose 82 can have a quasi conical head 120 with a three inch long one quarter inch long mouth opening. The opening can have a narrow elongated suction cup 122 at the opening.

As shown in FIGS. 9-11, the arm attachment can be a clear plastic hollow tube 122 with a latex membrane 142 with a center opening to receive arm or wrist at one end [this construction is similar to that of the thimble arrangement, but of course is larger]. A stainless steel hose clamp 144 can be used to provide sealing and/or tourniquet action. The other end of the tube can be threaded at 146 to be connected to hose 84.

As shown in FIG. 12, a conically shaped funnel 148 can be secured by a threaded end 150 to hose 86. The open mouth of the funnel can have a suitable seal 152.

Under certain conditions, it may be necessary to provide some type of cradle or other body support when the punch is placed into use.

While the invention has been described in detail with respect to preferred embodiments, the scope and ambit of the invention are defined by the terms of the claims which follow.

What is claimed is:

1. Apparatus for quickly removing contaminated tissue and blood from a localized skin wound of the body of a human being immediately after contamination has occurred, said apparatus comprising:
   a biopsy punch for removing all the tissue from the wound:
   first hose conduit means having one end connected to second means for having suction tight engagement with the wound and having an opposite end adapted to receive a force of suction, the second means including a plurality of separate elements, each one of said elements being adapted for detachable suction engagement with the body to treat a correspondingly different type of body wound, and a valve having a like plurality of input ports, each valve input port being connected to a corresponding element, the valve having a single output port connected to the one end of the first hose means, the valve being manually operable to select any one of the elements and to connect the selected one of the elements to the first hose means; and
   third means for producing said force of suction, the third means including a vacuum pump having an inlet port connected to the other end of the first means and having an outlet port, the contaminated blood from the wound being removed by suction through the selected element, the valve, the first hose means, and the pump and being discharged at the outlet port of the pump.

2. The apparatus of claim 1 further comprising:
   a wheeled cart supporting the first, second and third means, said cart also supporting a dc to ac power inverter, a dc power supply and an explosion proof motor, the motor being coupled to said pump, the supply being coupled through the inverter to the motor.

3. The apparatus of claim 1 wherein there are four elements, a first element being a finger/thumb suction thimble, a second element being an attachment for treating scratches or cuts, a third element being a funnel attachment, a fourth element being an arm attachment.

4. The apparatus of claim 1 further including a first filter connected between the valve output port and the one end of the first hose means.

5. The apparatus of claim 4 further including a second filter connected between the outlet port of the pump and a point of discharge.

* * * * *